United States Patent [19]

Koehler et al.

[11] Patent Number: 4,972,826

[45] Date of Patent: Nov. 27, 1990

[54] SHOCK WAVE GENERATOR FOR AN EXTRACORPOREAL LITHOTRIPSY APPARATUS

[75] Inventors: Goerg Koehler, Geisfeld; Arnim Rowhedder, Erlangen, both of Fed. Rep. of Germany

[73] Assignee: Siemens Aktiengesellschaft, Berlin and Munich, Fed. Rep. of Germany

[21] Appl. No.: 221,094

[22] Filed: Jul. 19, 1988

[30] Foreign Application Priority Data

Jul. 23, 1987 [DE] Fed. Rep. of Germany ... 8710118[U]

[51] Int. Cl.[5] .............................................. A61B 17/22

[52] U.S. Cl. ............................. 128/24 A; 128/663.01; 367/152

[58] Field of Search ................ 128/24 A, 328, 663.01; 367/150, 152, 175

[56] References Cited

U.S. PATENT DOCUMENTS 3,362,501 6/1968 Lenahan .

4,718,421 1/1988 Rohwedder et al. ............... 128/328

4,721,108 1/1988 Heine et al. ......................... 606/128

FOREIGN PATENT DOCUMENTS 0240797 10/1987 European Pat. Off. ............ 128/328

0131653 6/1989 European Pat. Off. .

88/03782 6/1988 PCT Int'l Appl. ................. 128/328

OTHER PUBLICATIONS

"Ultrasonics", vol. 7, No. 2, Apr. 1969, Acoustic Lens Design, pp. 98–100.

*Primary Examiner*—Kyle L. Howell

*Assistant Examiner*—Krista P. Pfaffle

*Attorney, Agent, or Firm*—Hill, Van Santen, Steadman & Simpson

[57] ABSTRACT

A shock wave generator for use in an extracorporeal lithotripsy apparatus has a liquid-filled housing with an exit aperture for shock waves which are electromagnetically generated and conducted to a focusing element for focusing onto the calculi, and a plate-shaped element having a smaller cross-sectional area than the emitted shock wave is disposed in the path propagation of the shock wave. The plate-shaped element consists of a material having an acoustic impedance substantially corresponding to the acoustic impedance of the liquid in the housing, and having a propagation speed of sound therein which deviates from the propagation speed of sound in the liquid.

17 Claims, 4 Drawing Sheets

SHOCK WAVE GENERATOR FOR AN EXTRACORPOREAL LITHOTRIPSY APPARATUS

BACKGROUND OF THE INVENTION

1. Field of the Invention

The present invention is directed to a shock wave generator for use in an extracorporeal lithotripsy apparatus of the type wherein a shock wave is generated, and is propagated in a liquid-filled housing and is focused onto the calculi by a focusing element in the shock wave generator.

2. Description of the Prior Art

Shock wave generators are known in the art which generate a shock wave or pressure wave front, and wherein a plate-shaped element is disposed in the shock wave generator between the origin of the shock wave and the shock wave exit. The plate-shaped element has a smaller transverse area (i.e., the area in a plane perpendicular to the propagation direction of the shock wave) than the shock wave and consists of a material having an acoustic impedance which deviates from the acoustic impedance of the liquid. Such a shock wave generator is described, for example, in German Patent No. 32 40 691. Because the transverse area of the plate-shaped element is smaller than that of the shock wave, a portion of the shock wave can pass by the plate-shaped member unimpeded, whereas another portion of the shock wave passes through the material of the plate-shaped member. Because the acoustic impedance of the material comprising the plate-shaped member is different form the acoustic impedance of the surrounding liquid, that portion of the shock wave interacting with the material of the plate-shaped member is multiplied into a sequence of shock wave fronts due to multiple reflections at the front and rear sides of the plate-shaped member. The chronological spacing between the shock wave fronts is critically dependent on the thickness of the plate-shaped member. These multiple shock wave fronts are superimposed on that portion of the shock wave which passes the plate-shaped member unimpeded, so that a number of shock wave fronts act on the calculus. The mechanical stresses respectively produced by these fronts are superimposed on the calculus, so that an improved disintegrating effect, in comparison to a single shock wave front, is achieved.

In this known shock wave generator, a pressure curve of the type shown in the example of FIG. 1 with respect to time, (the time axis being disposed at a level corresponding to atmospheric pressure, or some other nominal pressure) occurs at the focus of the shock waves. This is composed of a theoretically infinitely large number of pressure pulses generated by multiple reflections which follow each other in constant chronological spacings, pressure pulses **2*a* through 2*d* in FIG. 1 being shown by way of example. The amplitudes of these subsequent pressure pulses decrease in a geometrical series. A pressure pulse 1, corresponding to the aforementioned portion of the shock wave which did not interact with the material of the plate-shaped member, is superimposed on the pressure pulses 2*a* through 2*d*. Depending upon whether the speed of sound propagation in the liquid is lower or greater than the propagation speed of sound in the plate-shaped member, the pressure pulse 1 may lag or lead the pressure pulse 2*a*. The individual pressure pulses each exhibit an extremely steep rise and a substantially exponentional decay, generally concluding in an undershoot 3**, i.e., a considerable under-pressure briefly occurs under certain conditions. Such an undershoot can also exhibit the resultant chronological path of the pressure curve as a result of the addition of the pressure pulses. There are indications that the underpressure resulting from the drop in pressure in the region of the undershoot produces damage to the tissue surrounding the calculus which is to be destroyed. This damage is produced due to cavitation. Pressure curves which do not exhibit undershoots and are suitable for disintegrating calculi cannot be generated with the known shock wave generator as described above. Because of the multitude of pressure pulses which arise due to the multiple reflections, this known shock wave generator permits the chronological pressure curve at the focus to be modified only to a very limited degree. Another disadvantage of this known shock wave generator is that the multiple reflections at the boundary surfaces between the plate-shaped member and the liquid result in energy losses.

SUMMARY OF THE INVENTION

It is an object of the present invention to provide a shock wave generator wherein a chronologically varying pressure curve at the focus of the shock wave generator can be modified in substantial degree, and wherein energy losses due to boundary surface reflections are avoided.

The above objects are achieved in a shock wave generator of the type described above having a means for shaping the shock waves, such as a plate-shaped member, disposed in a liquid shock wave propagating medium and consisting of material having an acoustic impedance substantially corresponding to the acoustic impedance of the liquid in the shock wave generator, and in which the propagation speed of sound deviates from the propagation speed of sound in the liquid. The means for shaping has a transverse extent or area which is smaller than the transverse area of the shock waves, so that a portion of each shock wave interacts with the means for shaping, and a different portion of each shock wave passes, in the liquid, by the means for shaping substantially unimpeded. Because of the difference in the propagation speeds of sound in the plate-shaped member and in the liquid, a chronological delay between that portion of the shock wave which interacts with the material of the plate-shaped member and that portion of the shock wave which propagates exclusively in the liquid is present following the plate-shaped member. The portion of the shock wave which interacts with the material of the plate-shaped member either lags or leads the remaining, non-interacting portion of the shock wave, depending upon whether the propagation speed of sound in the plate-shaped member is lower or higher than in the liquid. A shock wave having a pressure front consisting of two chronogically offset crests of different amplitudes is thus present following the plate-shaped member. The chronological offset is dependent upon the relative propagation speeds of sound and the thickness of the plate-shaped member, the chronological offset being greater as the thickness increases and the more greatly the propagation speeds of sound deviate from each other. The relative amplitude difference between the crests is dependent on the difference between the areas of the interacting and non-interacting shock wave portions.

When such a shock wave converges at a focus, a chronological pressure curve as shown, for example, in the respective solid-line curves in FIGS. 2 and 3 can be achieved. Each solid line curve results from the combination of the dashed-line curve and the dot-and-dash curve shown in each Figures, which represent the interacting and non-interacting shock wave portions described above. A slight chronological offset of the crests of the resulting shock wave is present in the example of FIG. 2, so that the chronological pressure curve at the focus has two pressure peaks which follow each other in short succession, whereas a comparatively large chronological offset is present in the example of FIG. 3, so that the second pressure peak compensates the undershoot of the first portion of the shock wave. The height of the pressure peaks, moreover, is dependent on the transverse area of the interacting and non-interacting portions of the shock wave. The delayed, interacting portion of the shock wave in the example of FIG. 2 has a transverse area which is only slightly smaller in comparison to the non-interacting undelayed portion, whereas the transverse area of the delayed, interacting portion of the shock wave in the embodiment of FIG. 3 is considerably smaller than that of the non-interacting, undelayed part of the shock wave. Because the acoustic impedance of the plate-shaped member substantially corresponds to that of the liquid, it is insured that no significant reflections occur at the boundaries between those two media, so that the shock wave traverses the plate-shaped member with substantially no energy loss.

The shock wave source may be constructed so that the means for focusing the shock waves is an integrated portion of the shock wave source. For example, the shock wave source may have a suitably shaped emission face from which shock waves emanate already focused. If the shock wave source is of the type that a separate component, such as an acoustic lens or reflector, is needed for focusing the shock waves, the plate-shaped member can be disposed either between the origin of the shock waves and the means for focusing the shock waves, or following the means for focusing the shock waves in the shock wave propagation direction. It is also possible to provide plate-shaped members both between the shock wave origin and the means for focusing and after the means for focusing.

The plate-shaped member may have at least one opening in the region thereof traversed by the shock waves, and this opening may be centrally disposed in that region.

If the shock wave has a circular cross-section and if the plate-shaped member is to have a plurality of openings therein, the openings in the plate-shaped member may be sectors of a circle disposed in the region of the plate-shaped member traversed by the shock wave, with the tips of the openings lying on the center axis of the shock wave.

A wide range of variations in the chronological pressure curve at the focus can be achieved by using a plurality of plate-shaped members disposed in succession between the origin of the shock wave and the exit aperture of the shock wave generator. The regions of these plate-shaped members respectively traversed by the shock wave at least partially overlap, so that the plate-shaped members can be geometrically different and may consist of different materials. Further variations in the chronological pressure curve at the focus can be achieved by mounting the plate-shaped members so as to be individually rotatable relative to each other. A short structural length for the shock wave generator can be achieved in an embodiment wherein the surfaces of the plate-shaped members which face each other are disposed adjacent each other.

DESCRIPTION OF THE PREFERRED EMBODIMENTS

Figure 1:
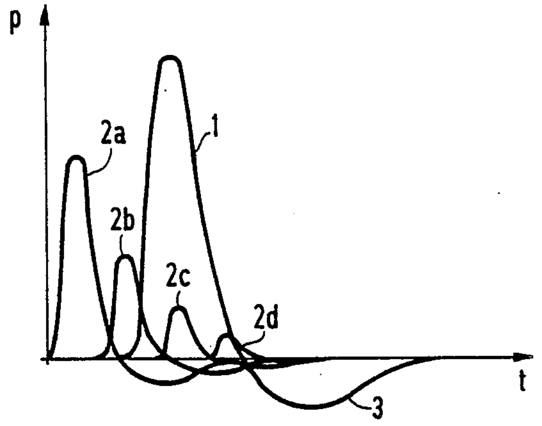
FIG 1 ( PRIOR ART )
FIG. 1 is a pressure/time curve of a shock wave in a shock wave generator constructed in accordance with the prior art.

As discussed above, FIG. 1 shows the typical chronological curve of the pressure at the focus of a shock wave generator constructed in accordance with the prior art. Although such a chronological pressure curve can normally successfully be used for disintegrating calculi, different chronological pressure curves are desirable in certain instances, as shown, for example, in FIGS. 2 and 3, which cannot be generated using prior art shock wave generators. The resultant chronological curve in FIG. 2 differs from the curve of FIG. 1 in that only two pressure peaks 4a and 4b following each other in immediate chronological succession are present. Such a pressure curve can result in high reliability in the disintegration of calculi, for certain types of calculi, because the calculus is first placed in a stressed condition by the first pressure peak 4a which "jolts"0 the calculus but does not disintegrate the calculus. The stress created by the second pressure peak 4b is then superimposed thereon, resulting in a more certain disintegration of the calculus. The resultant chronological pressure curve shown in solid lines in FIG. 3 differs from that of FIG. 1 in that the undershoot present in FIG. 1 is substantially absent in FIG. 3. A chronological pressure curve without such undershoots is desirable because such undershoots have under-pressure associated therewith, which can be considerable in certain circumstances, which can result in cavitation leading to damage of the tissue surrounding the calculus.

Figure 2:
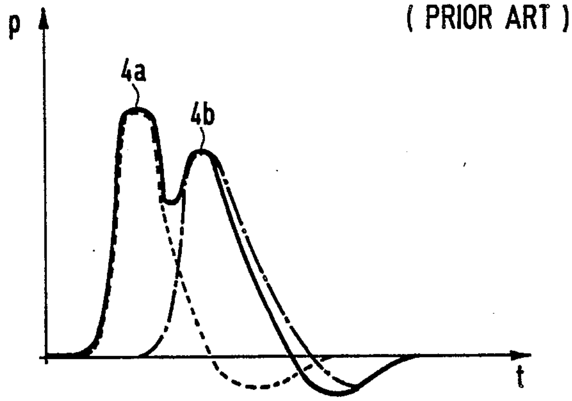
FIGS. 2 and 3 are examples of the pressure/time curves of the shock waves which can be achieved in a shock wave generator constructed in accordance with the principles of the present invention.
Figure 3:
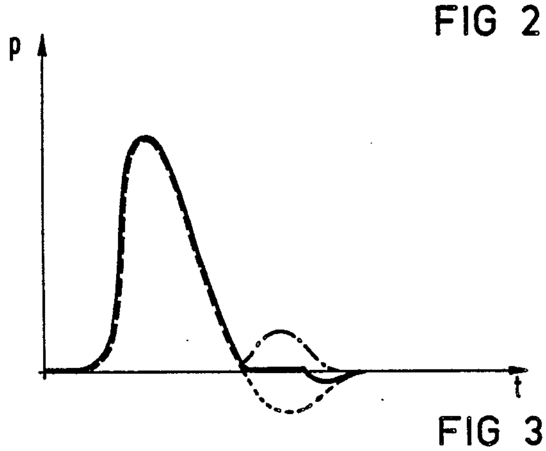
Figure 4:
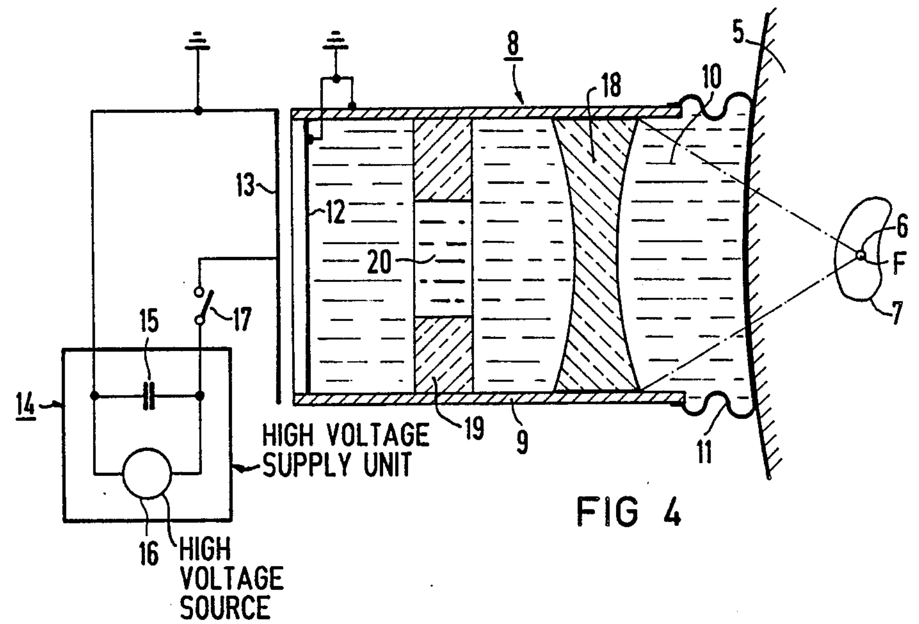
FIG. 4 is a side sectional view and a schematic circuit diagram for a shock wave generator constructed in accordance with the principles of the present invention in longitudinal section.

A shock wave generator constructed in accordance with the principles of the present invention which is capable of generating chronological pressure curves of the type shown in FIGS. 2 and 3 is shown in longitudinal section in FIG. 4. The shock wave generator is used to disintegrate a calculus 6 situated in a patient 5, for example, a stone in a kidney 7. The shock wave generator has a shock wave tube 8 consisting of a cylindrical housing filled with liquid, for example, water. The housing 9 has an exit aperture 10 for shock waves at one end thereof which is closed by a sack or bellows 11 permitting the shock wave tube 8 to be acoustically applied to the patient 5. The opposite end of the housing 9 is closed by a planar membrane 12, which forms a part of a means for generating the shock wave. The other components of the means for generating a shock wave are a flat coil 13, disposed adjacent the planar member 12, and high voltage supply unit 14. The high voltage supply unit 14 contains a capacitor 15 which can be charged to, for example, 20 kV with a high voltage source 16. When the capacitor 15 is connected to the flat coil 13 via a switch 17, the electrical energy stored in the capacitor suddenly discharges into the coil 13 and very rapidly generates a magnetic field. An oppositely directed current is induced in the membrane 12, which consists of electrically conductive material, so that an opposing magnetic field is also induced. Due to the interaction of the opposing fields, the membrane 12 is rapidly repelled from the coil 13, so that a unipolar shock wave is formed in the liquid contained within the housing 9.

To make this shock wave usable for disintegrating the calculus 6, the shock wave is focused by an acoustic lens 18 disposed in the housing 9. The lens 18 is disposed in the housing 9 so that its focus F coincides with the calculus 6. The shock wave which is coupled to the patient 5 via the sack 11 transfers a portion of its energy to the calculus 6, which is brittle in comparison to the surrounding tissue, and by so doing the shock wave exerts tensile and pressure forces on the calculus which decompose it into a number of particles which can be naturally eliminated.

To permit adjustment of the chronological pressure curve at the focus F of the shock wave generator, a plate-shaped member 19 is disposed between the membrane 12 and the focus F, more precisely between the membrane 12 and the acoustic lens 18. The plate-shaped member 19 consists of a material in which the propagation speed of sound deviates from the propagation speed of sound in the liquid, and having an acoustic impedance which substantially corresponds to the acoustic impedance of the liquid, so as to avoid reflections at the boundary surfaces with the liquid. In its region traversed by a shock wave emanating from the membrane 12, the plate-shaped member 19 has a transverse area which is smaller than the transverse area of the shock wave. This is achieved in the embodiment of FIG. 4 by providing the plate-shaped member 19 with a centrally disposed opening 20. After the planar shock wave emanating from the membrane 12 passes the location of the plate-shaped member 19, it consists of two portions which are chronologically offset relative to each other because one portion has interacted with the member 19, and the other portion has not. That portion of the shock wave passing through the opening 20 leads or lags that portion of the shock wave which interacted with the material of the plate-shaped member 19, depending upon whether the propagation speed of sound in the plate-shaped member 19 is lower or higher than that in the liquid. The chronological offset between the two portions of the shock wave increases as the difference in the propagation speeds of sound in the plate-shaped member and the liquid increases, and also increases with the thickness of the plate-shaped member 19.

After the chronologically offset portions of the shock wave are focused by the acoustic lens 18, a pressure curve as shown, for example, in FIG. 2, can be achieved having a slight chronological offset between the portions at the focus F, as can a chronological pressure curve as shown, for example, in FIG. 3 wherein the shock wave portions exhibit a relatively large chronological offset. The resultant chronological pressure curve is shown in solid lines in FIGS. 2 and 3, whereas the two pressure curves associated with the portions of the shock wave which are chronologically offset relative to each other are respectively shown with dashed lines and dot-and-dash lines. The height of the peaks of the offset portions of the shock wave depend on the respective transverse areas of the chronologically offset portions of the shock wave as they reach the focusing element 18, which are determined by the transverse area of the region of the plate-shaped member 19 which interacts with the shock wave, which in turn depends upon the transverse area of the opening 20. In the example of FIG. 2, both portions of the shock wave have substantially the same transverse area at the focus, whereas in the embodiment of FIG. 3 the trailing portion of the shock wave has a smaller cross-section in comparison to the remainder of the shock wave.

A multitude of different chronological pressure curves can be achieved by a suitable selection of the material and the thickness of the plate-shaped member 19, and by varying the relationship of the transverse area of the region of the member 19 traversed by the shock wave relative to the transverse area of the shock wave, i.e., by varying the size of the opening 20 in the embodiment of FIG. 4.

Figure 5:
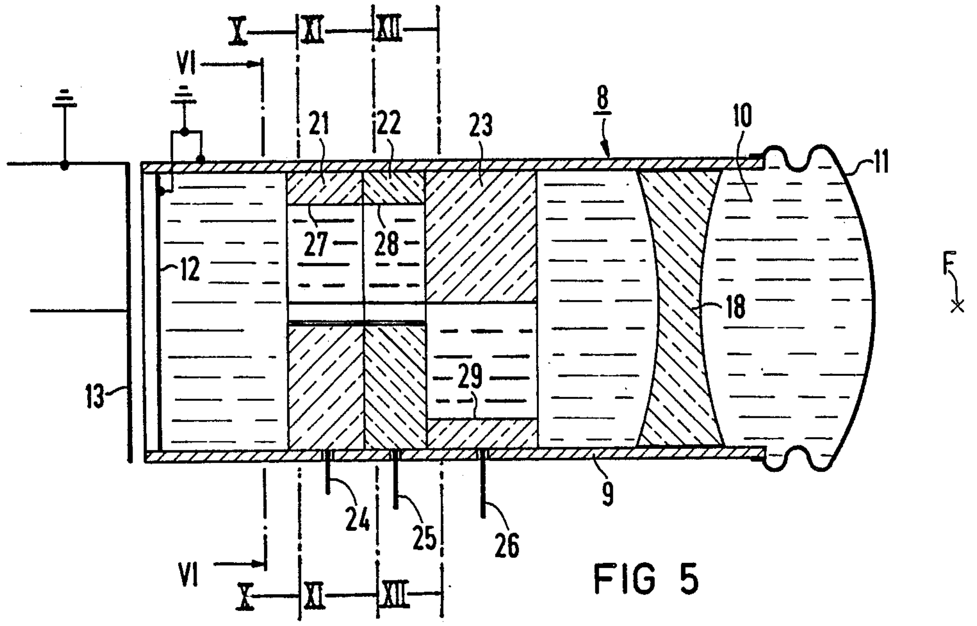
FIG. 5 is a side sectional view of a further embodiment of a shock wave generator constructed in accordance with the principles of the present invention in longitudinal section.

In the embodiment shown in FIG. 5, a shock wave generator has a plurality of plate-shaped members 21, 22 and 23 disposed between the membrane 12 and the focus F. As indicated by the different hatchings, the plate-shaped members 21, 22 and 23 may consist of respectively different materials, and may also have different thicknesses, i.e., may be geometrically different. The plate-shaped members 21, 22 and 23 are disposed so that the surfaces facing each other are disposed against each other. The plate-shaped members 21, 22 and 23 are, moreover, rotatably mounted in the tubular housing 9, the members being manually rotatable by respective adjustment levers 24, 25 and 26.

Figure 7:
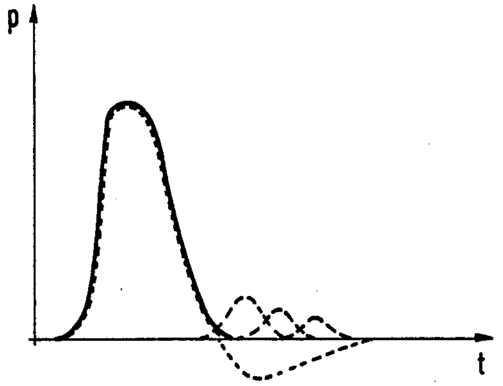
FIGS. 7 and 8 are examples of the pressure/time curve of a shock wave attainable in the shock wave generators of FIGS. 5 and 6.
Figure 8:
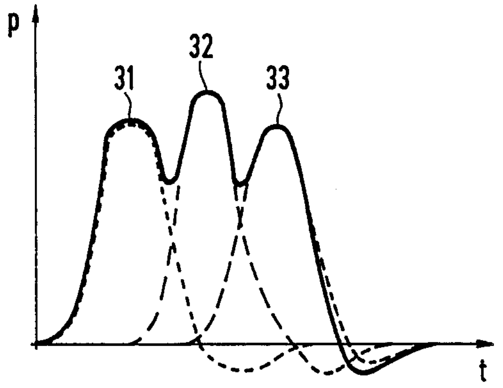

Pressure curves as shown in FIGS. 7 and 8 can be achieved at the focus F in the embodiment of FIG. 5, with the resultant chronological pressure curve, as in FIGS. 2 and 3, being shown with solid lines and the component pressure curves being shown in respective dashed and dot-and-dash lines. A chronological pressure curve is shown in FIG. 7 wherein the undershoot of the portion of the shock wave which arrives first at the focus F is substantially completely compensated by the following portions of the shock wave. FIG. 8 shows a chronological pressure curve having three successive pressure peaks 31, 32 and 33.

Figure 10:
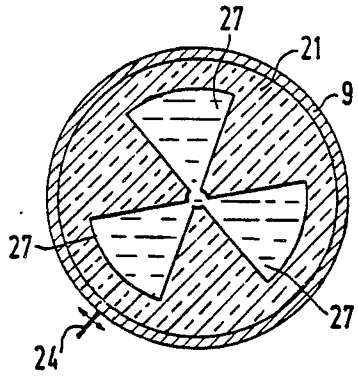
FIGS. 10, 11 and 12 are plan views of the plate-shaped members of FIG. 5, respectively taken along lines X—X, XI—XI and XII—XII of FIG. 5, preserving the relative orientation of the plates as shown in FIGS. 5 and 6.
Figure 11:
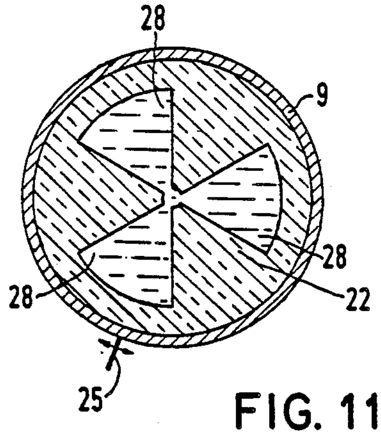
Figure 12:
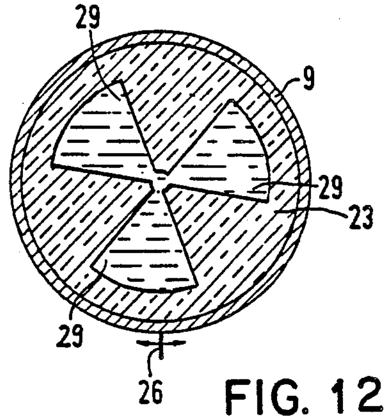

Plan views of the plate-shaped members 21, 22 and 23 shown in side sectional view in FIG. 5 are respectively shown in FIGS. 10, 11 and 12, with the plate-shaped members, 21, 22 and 23 being respectively oriented in FIGS. 10, 11 and 12 in the same position as in FIG. 5. These plates are shown superimposed in the view of FIG. 6, as "seen" by the incoming shock wave (i.e., a view taken along line VI—VI of FIG. 5). Consequently, the upstream-most plate-shaped member 21 can be seen in its entirety, and plate-shaped members 22 and 23 are superimposed, rotationally offset, behind the plate-shaped member 21. The sector-shaped openings of the plate-shaped member 21 are thus shown in solid lines in FIG. 6, and given the orientation of the plate-shaped members 21, 22 and 23 shown in FIGS. 10, 11 and 12, portions of the plate-shaped members 22 and 23 can be seen through the openings in the plate 21 in FIG. 6. The dashed lines in FIG. 6 represent the remainder of the respective openings in plate-shaped members 22 and 23, which cannot be directly seen due to the presence of the plate-shaped member 21.

Figure 6:
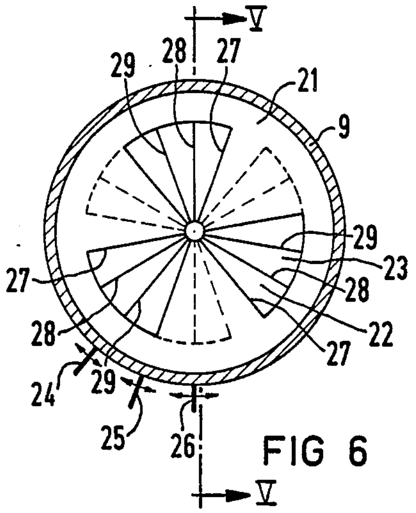
FIG. 6 is a sectional view taken along line VI—VI in FIG. 5.

As shown in FIG. 6, by rotationally adjusting the plate-shaped members 21, 22 and 23 by means of the levers 24, 25 and 26, the respective openings 27, 28 and 29 therein can be made to overlap in varying amounts. The openings 27, 28 and 29 may be in the form of sectors of a circle, having tips coinciding with the central axis of the shock wave.

Figure 9:
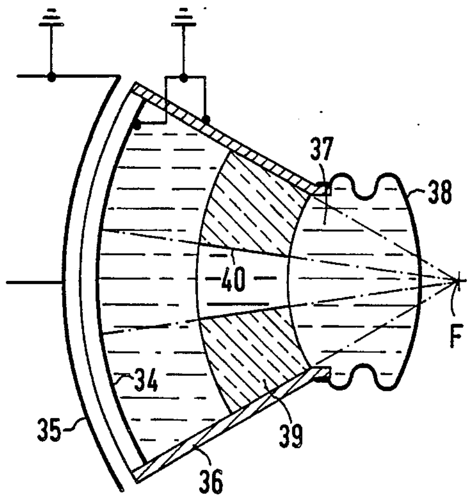
FIG. 9 is a side sectional view of a further embodiment of a shock wave generator constructed in accordance with the principles of the present invention in longitudinal section.

In the embodiment shown in FIG. 9, a shock wave generator has a membrane 34 which is spherically curved, and a correspondingly curved coil 35 is disposed opposite the membrane 34. The membrane 34 terminates a housing 36 in the form of a truncated cone. At the opposite end of the housing 36, the exit aperture 37 is closed by a bellows or sack 38, again permitting acoustic application of the shock wave generator to a patient. The shock wave generator is filled with liquid. In the embodiment of FIG. 9, separate structure for focusing the shock waves originating at the membrane 34 is not needed, because the shock wave generated by the membrane 34 is already concentrated at the focus F, which corresponds to the center of curvature of the spherical membrane 34. The membrane 34 thus assumes the function of the means for focusing the shock waves. A plate-shaped member 39 is disposed between the membrane 34 and the focus F. The plate-shaped member 39 consists of material having an acoustic impedance substantially corresponding to the acoustic impedance of the liquid, and having a propagation speed of sound therein which deviates from the propagation speed of sound in the liquid. The plate-shaped member 39 is spherically curved as the membrane 34, the center of curvature of the plate-shaped member 39 coinciding with that of the membrane 34. The center of the plate-shaped member 39 has an opening 40, also in the form of a truncated cone, and having an aperture angle so that its imaginary tip coincides with the center of curvature of the membrane 34 and the plate-shaped member 39, i.e., with the focus F. Chronological pressure curves at the focus F of the type shown in FIGS. 2 and 3 can be achieved with the shock wave generator of FIG. 9.

The exemplary embodiments described above have been shown only in the context of the electromagnetic generation of shock waves using a rapidly repelled membrane. The inventive concept disclosed herein may, however, be used in shock wave generators wherein the shock wave is produced by other means, for example wherein the shock waves are generated by underwater spark discharge, wherein the shock waves are piezoelectrically generated, or wherein the shock waves are generated by the interraction of a laser beam with a highly absorbent object situated in the liquid. The plate-shaped members may also assume different shapes than shown in the exemplary embodiments, particularly the shape of the openings therein. The only requirement is that the shape, including the opening, be suited to achieve a shock wave having the desired composition of chronologically offset portions.

Although modifications and changes may be suggested by those skilled in the art it is the intention of the inventors to embody within the patent warranted hereon all changes and modifications as reasonably and properly come within the scope of their contribution to the art.

What is claimed is:

1. A shock wave generator for extracorporeal disintegration of a calculus in a patient comprising:
 a housing;
 a shock wave conducting medium filling said housing and having a propagation speed of sound therein and an acoustic impedance;
 means connected to said housing for generating a shock wave propagating in said shock wave conducting medium along a propagation path, said shock wave having a transverse area in a plane perpendicular to said propagation path;
 means in said housing for focusing said shock wave at a calculus in a patient; and
 means disposed in said housing in said propagation path for shaping said shock wave to a shape adapted to disintegrate said calculus, said means for shaping acoustically coupled to said housing, said means for shaping having a transverse area in said plane perpendicular to said propagation path which is smaller than said transverse area of said shock wave so that a portion of said shock wave interacts with said means for shaping and a different portion of said shock wave propagates, in said medium, substantially unimpeded past said means for shaping, a propagation speed of sound therein different from said propagation speed of sound in said shock wave conducting medium, and an acoustic impedance substantially equal to said acoustic impedance of said shock wave conducting medium.

2. A shock wave generator as claimed in claim 1, wherein said means for shaping said shock wave is a plate-shaped member having a region traversed by said shock wave and having at least one opening in said region.

3. A shock wave generator as claimed in claim 2, wherein said plate-shaped member has a centerally disposed opening.

4. A shock wave generator as claimed in claim 2, wherein said shock wave has a center axis, and wherein said opening in said plate-shaped member is a sector of a circle, said sector having a tip on said center axis.

5. A shock wave generator as claimed in claim 2, wherein said shock wave has a center axis, and wherein said plate-shaped member has a plurality of openings therein, each of said openings being a sector of a circle and each having a tip on said central axis.

6. A shock wave generator as claimed in claim 1, wherein said means for shaping said shock wave comprises a plurality of plate-shaped members disposed in succession along said propagation path.

7. A shock wave generator as claimed in claim 6, wherein each of said plate-shaped members is geometrically different.

8. A shock wave generator as claimed in claim 6, wherein each of said plate-shaped members has a different thickness along said propagation path.

9. A shock wave generator as claimed in claim 6, wherein each of said plate-shaped members has an opening therein.

10. A shock wave generator as claimed in claim 9, wherein said openings are respectively disposed in said plate-shaped members so as to at least partially overlap in said propagation path.

11. A shock wave generator as claimed in claim 10, wherein said shock wave has a center axis, and wherein said shock wave generator further comprises means for independently rotating each of said plate-shaped members around said center axis.

12. A shock wave generator as claimed in claim 11, wherein each of said openings in said plate-shaped members is a sector of a circle having a tip at said center axis.

13. A shock wave generator as claimed in claim 6, wherein said plate-shaped members are disposed adjacent each other in succession.

14. A shock wave generator as claimed in claim 1, wherein said means for focusing is an acoustic lens, and wherein said means for shaping said shock wave is disposed between said means for generating a shock wave and said means for focusing.

15. A shock wave generator for extracorporeal disintegration of a calculus in a patient comprising:

a housing;

a shock wave conducting medium filling said housing and having a propagation speed of sound therein and an acoustic impedance;

means connected to said housing for generating a shock wave propagating in said shock wave conducting medium along a propagation path;

means for focusing said shock wave at a calculus in a patient; and a plate disposed in said housing in said propagation path, said plate having a region traversed by said shock wave and having an opening in said region filled with said medium so that a portion of said shock wave interacts with said plate and a different portion of said shock wave propagates, in said medium, past said plate substantially unimpeded, said plate consisting of material having a propagation speed of sound therein different from said propagation speed of sound in said shock wave conducting medium and having an acoustic impedance substantially equal to said acoustic impedance of said shock wave wave is given a shape adapted to disintegrate said calculus.

16. A shock wave generator for extracorporeal disintegration of a calculus in a patient comprising:

a housing;

a shock wave conducting medium filling said housing and having a propagation speed of sound therein and an acoustic impedance;

means connected to said housing for generating a shock wave propagating in said shock wave conducting medium along a propagation path, said shock wave having a center axis;

means adapted for focusing said shock wave at a calculus in a patient;

a plurality of plate-shaped elements disposed in succession in said housing in said propagation path, each of said plate-shaped elements having a region traversed by said shock wave, said regions overlapping, and each of said elements having an opening, filled with said medium in said region so that a portion of said shock wave interacts with each of said elements and at least one different portion of said shock wave propagates in said openings, and each of said elements having a propagation speed of sound therein different from said propagation speed of sound in said shock wave conducting medium and an acoustic impedance substantially equal to said acoustic impedance of said shock wave conducting medium; and means for independently rotating each of said elements around said center axis to selectively orient said openings relative to each other.

17. A shock wave generator as claimed in claim 16, wherein each of said openings in said elements is a sector of a circle having a tip on said center axis.

* * * * *